United States Patent
Morikawa et al.

(10) Patent No.: US 6,720,458 B2
(45) Date of Patent: Apr. 13, 2004

(54) PHOTOOXIDATION CATALYST AND PRODUCTION PROCESS FOR ALDEHYDE DERIVATIVES

(75) Inventors: Kohei Morikawa, Kawasaki (JP); Shunichi Fukuzumi, Toyonaka (JP); Kei Ohkubo, Ibaraki (JP); Yutaka Ohnishi, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/235,834

(22) Filed: Sep. 6, 2002

(65) Prior Publication Data

US 2003/0098229 A1 May 29, 2003

Related U.S. Application Data

(60) Provisional application No. 60/318,318, filed on Sep. 12, 2001.

(30) Foreign Application Priority Data

Sep. 7, 2001 (JP) ........................................ 2001-272352

(51) Int. Cl.$^7$ ........................ C07C 45/36; C07C 255/00
(52) U.S. Cl. ........................ 568/436; 558/411; 558/425
(58) Field of Search ................. 558/411, 425; 568/436

(56) References Cited

U.S. PATENT DOCUMENTS 4,684,734 A * 8/1987 Kaieda et al.

FOREIGN PATENT DOCUMENTS

| JP | 60-166655 A | 8/1985 |
|----|-------------|--------|
| JP | 09-227490 A | 9/1997 |

OTHER PUBLICATIONS

Ohkubo, et al., 100¢ Selective Oxygenation of p–Xylene to p–Tolualdehyde via Photoinduced Electron Transfer, Organic Letters, vol. 2, No. 23, pp. 3647–3650 (2000).
Rapoport, et al., "The Hydrolysis of Some Cyanocinnamic Acids", J. Am. Chem. Soc., 75, pp. 1125–1129 (1953).
Patent Abstracts of Japan, abstracting JP 60–166655, Aug. 29, 1985.
Patent Abstracts of Japan, abstracting JP 09–227490, Sep. 2, 1997.

\* cited by examiner

Primary Examiner—Shailendra Kumar
Assistant Examiner—Sikarl A. Witherspoon
(74) Attorney, Agent, or Firm—Sughrue Mion, PLLC

(57) ABSTRACT

The present invention relates to a catalyst useful for a photooxidation reaction and also relates to a novel process for producing aldehydes, particularly aromatic aldehydes, which are useful as an intermediate for the production of agrochemical and medical preparations. The catalyst is particularly suitable for the oxidation of a methyl group difficult to oxidize.

A photooxidation catalyst according to the invention is a halogenated aromatic nitrile represented by the following formula (1):

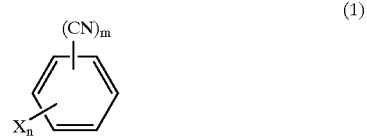

(1)

(wherein X represents a chlorine atom or a fluorine atom, m represents an integer of 1 to 5, n represents an integer of 1 to 5, m+n≦6, and when n is 2 or more, Xs may be the same or different).

7 Claims, No Drawings

PHOTOOXIDATION CATALYST AND PRODUCTION PROCESS FOR ALDEHYDE DERIVATIVES

RELATED APPLICATION REFERENCE

This application is an application filed under 35 U.S.C. §111(a) claiming benefit pursuant to 35 U.S.C. §119(e)(1) of the filing date of Provisional Application No. 60/318,318 filed Sep. 12, 2001 pursuant to 35 U.S.C. §111(b).

FIELD OF THE INVENTION

The present invention relates to a catalyst useful for a photooxidation reaction and also relates to a novel process for producing aldehydes, particularly aromatic aldehydes, which are useful as an intermediate for the production of agrochemical and medical preparations. The catalyst is particularly suitable for the oxidation of a methyl group difficult to oxidize.

BACKGROUND ART

The production method of aldehydes is generally not easy and various methods are being studied, such as oxidation of methyl group, reduction of carboxylic acid and reductive hydrolysis of nitrile. Particularly, according to the method of oxidizing a methyl group, the oxidation reaction terminates at the stage of an alcohol or continues until the production of a carboxylic acid in many cases and it is difficult to stop the reaction at the stage of an aldehyde by a general oxidation method.

The production process for aldehydes is described by referring to the case of producing cyanobenzaldehydes. Several methods for the production of cyanobenzaldehydes are known.

For example, J. Am. Chem. Soc., 75, 1125 (1953) discloses a method of reducing cyanobenzoyl chloride by the Rosenmund reduction. JP-A-60-166655 (the term "JP-A" as used herein means an "unexamined published Japanese patent application") discloses a method of reacting p-cyanobenzyl chloride with hexamethylenetetramine in an oil-water two-layer system. JP-A-9-227490 discloses a method of reacting dichloromethylbenzonitrile with morpholine and then hydrolyzing the reactant.

These methods all involve generation of a large amount of wastes and cannot be an industrially excellent production process.

A photooxidation reaction using a catalyst is a conventionally known method. For example, as for the method of converting a toluene into an aromatic aldehyde by a photooxidation reaction, Org. Lett. 2000, 2, 3647 discloses a method of oxidizing p-xylene with an oxygen using 9-phenyl-10-methylacridinium as a photocatalyst to produce p-tolualdehyde. However, this catalyst is not inexpensive and not easily available.

One object of the present invention is to provide a catalyst useful for a photooxidation reaction. Another object of the present invention is to provide means for producing aromatic aldehydes which are useful as an intermediate in the production of agrochemical and medical preparations, by an industrially advantageous method.

SUMMARY OF THE INVENTION

The present invention relates to the following matters.

[1] A photooxidation catalyst which is a halogenated aromatic nitrile represented by the following formula (1):

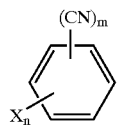

(1)

(wherein X represents a chlorine atom or a fluorine atom, m represents an integer of 1 to 5, n represents an integer of 1 to 5, $m+n \leq 6$, and when n is 2 or more, Xs may be the same or different).

[2] The photooxidation catalyst as described in [1], wherein the halogenated aromatic nitrile is at least one selected from the group consisting of tetrafluoroterephthalonitrile, tetrafluoroisophthalonitrile and tetrafluorophthalonitrile.

[3] The photooxidation catalyst as described in [2], wherein the halogenated aromatic nitrile is tetrafluoroterephthalonitrile.

[4] The photooxidation catalyst as described in any one of [1] to [3], wherein the catalyst is used for photooxidation reaction of converting a methyl group into an aldehyde group.

[5] The photooxidation catalyst as described in any one of [1] to [3], wherein the catalyst is used for photooxidation reaction of converting a methyl group of methyl group-substituted aromatics into an aldehyde group.

[6] The photooxidation catalyst as described in any one of [1] to [3], wherein the catalyst is used for photooxidation reaction of converting a methyl group of methylbenzene derivatives into an aldehyde group.

[7] The photooxidation catalyst as described in any one of [1] to [3], wherein the catalyst is used for photooxidation reaction of converting a methylbenzene represented by formula (2):

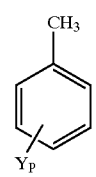

(2)

(wherein Y represents a chlorine atom, a fluorine atom, a cyano group, a nitro group, a hydroxyl group, a carboxyl group, an alkyl group having from 1 to 4 carbon atoms which may have a substituent, an alkoxy group having from 1 to 4 carbon atoms which may have a substituent, or an aldehyde group, p represents an integer of 0 to 5, and when p is 2 or more, Ys may be the same or different) to a benzaldehyde represented by formula (3):

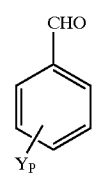

(3)

(wherein Y represents a chlorine atom, a fluorine atom, a cyano group, a nitro group, a hydroxyl group, a carboxyl group, a sulfonic acid group, an alkyl group having from 1 to 4 carbon atoms which may have a substituent, an alkoxy group having from 1 to 4 carbon atoms which may have a substituent, or an aldehyde, p represents an integer of 0 to 5, when p is 2 or more, Ys may be the same or different).

[8] A process for producing aldehydes, comprising photooxydizing a methyl group into an aldehyde group in the presence of the photooxidation catalyst as described in any one of [1] to [3].

[9] The process for producing aldehydes as described in [8], wherein the methyl group is a methyl group of methyl group-substituted aromatics, and thereby producing an aromatic aldehyde.

[10] The process for producing aldehydes as described in [9], wherein the methyl group of methyl group-substituted aromatics is a methyl group of methylbenzene, and thereby producing a benzaldehyde.

[11] The process for producing aldehydes as described in [10], wherein the methylbenzene is represented by formula (2):

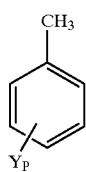

(2)

(wherein Y represents a chlorine atom, a fluorine atom, a cyano group, a nitro group, a hydroxyl group, a carboxyl group, an alkyl group having from 1 to 4 carbon atoms which may have a substituent, an alkoxy group having from 1 to 4 carbon atoms which may have a substituent, or an aldehyde group, p represents an integer of 0 to 5, and when p is 2 or more, Ys may be the same or different), and by photooxydizing the methyl group of said methylbenzene, thereby producing a benzaldehyde represented by formula (3):

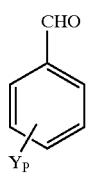

(3)

(wherein Y represents a chlorine atom, a fluorine atom, a cyano group, a nitro group, a hydroxyl group, a carboxyl group, a sulfonic acid group, an alkyl group having from 1 to 4 carbon atoms, which may have a substituent, an alkoxy group having from 1 to 4 carbon atoms, which may have a substituent, or an aldehyde, p represents an integer of 0 to 5, when p is 2 or more, Ys may be the same or different).

BEST MODE FOR CARRYING OUT THE INVENTION

The present invention is described in detail below. Halogenated aromatic nitrites as the catalyst for use in the present invention are put on the market and easily available. In formula (1), the nitrile group and the halogen are not limited on the number of bonds and the position of bonding. Examples of the halogen include chlorine and fluorine.

Specific examples of the halogenated aromatic nitrites represented by formula (1) include tetrafluorophthalonitile, tetrafluoroisophthalonitrile, tetrafluoroterephthalonitrile, pentafluorobenzonitrile, 2,3,5,6-tetrafluorobenzonitrile, 2,3,4,6-tetrafluorobenzonitrile, 2,3,4,5-tetrafluorobenzonitrile, 2,4,6-trifluoro-5-chloroisophthalonitrile, tetrachlorophthalonitrile, tetrachloroisophthalonitrile and tetrachloroterephthalonitrile. Among these, preferred are tetrafluorophthalonitrile, tetrafluoroisophthalonitrile and tetrafluoroterephthalonitrile, more preferred is tetrafluoroterephthalonitrile.

These halogenated aromatic nitrites may be used individually or in combination of two or more thereof.

The photooxidation reaction is performed by applying light in the presence of an oxygen and a photooxidation catalyst. If the oxidizing power of the photooxidation catalyst is low, the oxidation reaction does not proceed, whereas if it is excessively high, a side reaction takes place and the selectivity decreases.

The light applied is not particularly limited on the wavelength and the irradiation means, however, a mercury lamp or a xenon lamp is generally used.

The photooxidation catalyst of the present invention can be used for various oxidations of substrates over a wide range. When the photooxidation catalyst is used for the oxidation of a methyl group, aldehyde can be produced with good selectivity. In particular, the photooxidation catalyst is preferably used for the oxidation of a methyl group substituted on an aromatic ring, preferably for oxidizing a methyl group relatively difficult to oxidize, into an aldehyde. The photooxidation catalyst is more preferably used for the reaction of converting an ortho-, meta- or para-substituted tolunitrile into a cyanobenzaldehyde.

Examples of the methyl group-substituted aromatics as the substrate include toluene, o-cresol, m-cresol, p-cresol, 2-methylanisole, 3-methylanisole, 4-methylanisole, p-toluenesulfonic acid, o-tolunitrile, m-tolunitrile, p-tolunitrile, o-methylbenzoic acid, m-methylbenzoic acid, p-methylbenzoic acid, halogenated methylbenzene, 1-methylnaphthalene, 2-methylnaphthalene, α-picoline, β-picoline, γ-picoline, 2-methylfuran, 2-methylthiophene, 3-methylthiophene, 1-methylpyrrole, 2-methylpyrrole, methylpyrazine, methylpyridazine, methylpyrimidine and methyltriazine.

In the reaction of the present invention, even if two or more methyl groups are present on one substrate, when one methyl group is oxidized, there arises a change in the oxidation/reduction potential between the product and the starting material. Therefore, when the reaction of the present invention is applied to compounds having two or more methyl groups, such as xylene derivatives, or compounds having a methyl group and an alkyl group, it is possible to selectively oxidize one methyl group.

In the present invention, a solvent generally used for the photooxidation reaction may be used. It is also possible not to use a solvent. For example, in the case of converting a tolunitrile into a cyanobenzaldehyde, the tolunitrile may be used in place of the solvent and recovered by separation after the reaction.

The reaction of the present invention may be performed by supplying an oxygen to be previously present in the reaction system or while blowing an oxygen into the reaction system.

The amount used of the halogenated aromatic nitrile as the catalyst of the present invention is, although not particularly limited to, preferably 10 molar times or less that of the substrate, more preferably from 0.01 mol % to 2 molar times that of the substrate. When the aromatic nitrile is used for the photooxidation reaction, it is generally deactivated by the coupling with the substrate. This coupling reaction hardly occurs in the use of the halogenated aromatic nitrile so that an optimal amount thereof varies depending on the substrate and the catalyst.

The halogenated aromatic nitriles as the catalyst, the benzaldehydes as the product and the methylbenzenes as the raw material of the present invention can be separated by using differences in solubility in a solvent. The solvent used herein is not particularly limited as far as it can dissolve the benzaldehydes as the product without reaction therewith and if it has low solubility with the halogenated aromatic nitrile. Examples of the preferable solvents include aliphatic hydrocarbons, such as pentane, hexane, heptane, cyclohexane and methylcyclohexane, and aromatic hydrocarbons, such as benzene, toluene, o-xylene, m-xylene, p-xylene, ethylbenzene and cumene. Of these, benzene and toluene are particularly preferable in view of solubility difference and after-treatment simplicity.

When the treatment temperature is too high, the solubility of the halogenated aromatic nitrile unfavorably increases to impair ability of separation, and, when it is too low, the solubility of the benzaldehyde as the product too unfavorably decreases to necessitate further addition of the solvent to avoid deposition. The treatment temperature is preferably 0 to 60° C., particularly preferably 10 to 40° C.

The solvent is used in such an amount that the resulting benzaldehyde can be completely dissolved therein, but can be used in an increased amount when the resulting benzaldehyde attach to the deposited halogenated aromatic nitrile to decrease its yield. Generally the solvent is used in amounts of preferably 1 to 100 times by mass, more preferably 2 to 50 times by mass the raw material methylbenzene.

To isolate and purify the resulting benzaldehyde from the solution after removal of the halogenated aromatic nitrile, the solvent can be subjected to distillation and concentration, followed by recrystallization of the product, or the solvent can be distilled under reduced pressure, followed by isolation of the product.

For example, when the reaction is carried out with the raw material of p-tolunitrile, the p-tolunitrile as the raw material has a boiling point of 103 to 106° C. (20 Torr), whereas p-tolualdehyde as the product has a boiling point of 133° C. (12 Torr) and p-cyanobenzyl alcohol as a by-product has a boiling point of 130° C. (5 Torr) so that isolation and purification can be made by vacuum distillation.

EXAMPLES

The present invention is described below by referring to Examples.

Example 1

In an NMR tube were enclosed 0.6 mL of acetonitrile saturated with oxygen, 2.1 mg (30 mM) of p-tolunitrile and 1.2 mg (10 mM) of 2,3,5,6-tetrafluoroterephthalonitrile. Then light was applied thereto at room temperature using a high-pressure mercury lamp. The conversion and yield with the passage of 1, 2, 4 or 8 hours after the initiation of light irradiation were measured by $^1$H NMR and the results obtained are shown in Table 1. Products other than p-cyanobenzaldehyde (hereinafter referred to as "CBAD") and p-cyanobenzyl alcohol (hereinafter referred to as "CBAL") were not detected.

TABLE 1

| Reaction Time (hour) | Conversion (%) | Yield (%) CBAD | Yield (%) CBAL |
|---|---|---|---|
| 1 | 6 | 6 | 0 |
| 2 | 9 | 8 | 1 |
| 4 | 18 | 15 | 3 |
| 8 | 27 | 22 | 4 |

Example 2

A reactant mixture was prepared by dissolving 0.126 g (1 mmol) of o-chlorotoluene, and 0.200 g (1 mmol) of 2,3,5,6-tetrafluoroterephthalonitrile in 100 mL of acetonitrile saturated with oxygen. 2 mL of the reactant mixture was transferred into a UV-measuring quartz cell, which was then tightly stoppered, and light was applied thereto at room temperature for 8 hours using a high-pressure mercury lamp. Analysis by gas-chromatography gave an o-chlorotoluene conversion of 38% and an o-chlorobenzaldehyde yield of 18%.

Example 3

Example 2 was repeated, except that the o-chlorotoluene was replaced by methyl p-methylbenzoate, 0.150 g (1 mmol). Analysis by gas-chromatography gave a methyl p-methylbenzoate conversion of 50% and a methyl p-formylbenzoate yield of 18.5%.

Example 4

To a 500-mL glass photoreactor equipped with an agitating function by a magnetic stirrer were added 300 mL of oxygen-saturated acetonitrile, 0.35 g (3 mmol) of p-tolunitrile and 0.60 g (3 mmol) of 2,3,5,6-tetrafluoroterephthalonitrile, and light was applied thereto at room temperature with stirring for 28 hours using a high-pressure mercury lamp. Analysis by gas-chromatography gave a p-tolunitrile conversion of 75% and a CBAD yield of 30%.

Example 5

The reaction liquid obtained in Example 4 was concentrated and dried into a solid by means of an evaporator. This concentrating operation was repeated 30 times.

The resulting residues were collected in a 100-mL eggplant type flask, to which 25 g of toluene was further added, and the mixture was agitated at room temperature for 1 hour. After the agitation, the solid matters were filtered out and the filtrate was distilled to remove the toluene by an evaporator and then vacuum distilled, thereby 3.5 g of CBAD was obtained.

EFFECT OF THE INVENTION

According to the present invention, a catalyst useful for a photooxidation reaction, which is represented by formula (1), is provided. By using this catalyst, aldehydes, particularly aromatic aldehydes can be produced advantageously in industry.

What is claimed is:

1. A method of photooxidation of a substrate comprising reacting the substrate with oxygen by applying light in the presence of a halogenated aromatic nitrile photooxidation catalyst represented by the following formula (1):

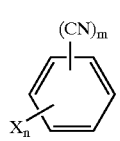
(1)

(wherein X represents a chlorine atom or a fluorine atom, m represents an integer of 1 to 5, n represents an integer of 1 to 5, $m+n \leq 6$, and when n is 2 or more, Xs may be the same or different).

2. The method as claimed in claim 1, wherein the halogenated aromatic nitrile is at least one selected from the group consisting of tetrafluoro-terephthalonitrile, tetrafluoroisophthalonitrile and tetrafluorophthalonitrile.

3. The method as claimed in claim 2, wherein the halogenated aromatic nitrile is tetrafluoro-terephthalonitrile.

4. A process for producing aldehydes, comprising photooxidizing a methyl group into an aldehyde group in the presence of a photooxidation catalyst which is a halogenated aromatic nitrile represented by the following formula (1):

(1)

(wherein X represents a chlorine atom or a fluorine atom, m represents an integer of 1 to 5, n represents an integer of 1 to 5, $m+n \leq 6$, and when n is 2 or more, Xs may be the same or different).

5. The process for producing aldehydes as claimed in claim 4, wherein the methyl group is a methyl group of methyl group-substituted aromatics, and thereby producing an aromatic aldehyde.

6. The process for producing aldehydes as claimed in claim 5, wherein the methyl group of methyl group-substituted aromatics is a methyl group of methylbenzene, and thereby producing a benzaldehyde.

7. The process for producing aldehydes as claimed in claim 6, wherein the methylbenzene is represented by formula (2):

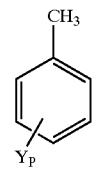
(2)

(wherein Y represents a chlorine atom, a fluorine atom, a cyano group, a nitro group, a hydroxyl group, a carboxyl group, an alkyl group having from 1 to 4 carbon atoms which may have a substituent, an alkoxy group having from 1 to 4 carbon atoms which may have a substituent, or an aldehyde group, p represents an integer of 0 to 5, and when p is 2 or more, Ys may be the same or different), and by photooxidizing the methyl group of said methylbenzene, thereby producing a benzaldehyde represented by formula (3):

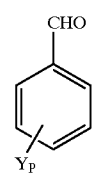
(3)

(wherein Y represents a chlorine atom, a fluorine atom, a cyano group, a nitro group, a hydroxyl group, a carboxyl group, a sulfonic acid group, an alkyl group having from 1 to 4 carbon atoms, which may have a substituent, an alkoxy group having from 1 to 4 carbon atoms, which may have a substituent, or an aldehyde, p represents an integer of 0 to 5, when p is 2 or more, Ys may be the same or different).

* * * * *